United States Patent [19]

Livingston et al.

[11] Patent Number: 4,692,412

[45] Date of Patent: Sep. 8, 1987

[54] METHOD OF PREPARING AN AUTOGENOUS VACCINE

[76] Inventors: Virginia W. Livingston, 8492 Prestwick Dr., LaJolla, Calif. 92037; Eleanor G. Alexander-Jackson, 390 Riverside Dr., New York, N.Y. 10025; Afton M. Livingston, 8492 Prestwick Dr., LaJolla, Calif. 92037

[21] Appl. No.: 839,457

[22] Filed: Mar. 11, 1986

Related U.S. Application Data

[63] Continuation of Ser. No. 569,253, Jan. 9, 1984, abandoned, which is a continuation of Ser. No. 171,543, Jul. 23, 1980, abandoned, which is a continuation of Ser. No. 955,878, Oct. 30, 1978, abandoned, which is a continuation of Ser. No. 776,360, Mar. 10, 1977, abandoned, which is a continuation of Ser. No. 672,965, Apr. 2, 1976, abandoned, which is a continuation of Ser. No. 295,720, Oct. 6, 1972, abandoned, which is a continuation-in-part of Ser. No. 82,806, Oct. 21, 1970, abandoned, which is a continuation-in-part of Ser. No. 831,985, Jun. 10, 1969, abandoned, which is a continuation-in-part of Ser. No. 490,629, Sep. 27, 1965, abandoned.

[51] Int. Cl.[4] .................... C12N 1/20; A61K 39/085
[52] U.S. Cl. ....................... 435/253; 424/92
[58] Field of Search ............ 435/68, 253, 170; 424/92

[56] References Cited

PUBLICATIONS

Livingston et al., Trans. N.Y. Ac. Sci, Series II, vol. 33, May 1972.
Cantwell et al., Arch. Derm., vol. 104, Jul. 1971, pp. 21-25.
Alexander-Jackson, Growth, vol. 30, 1966, pp. 199-228.
Livingston et al., Ann. N.Y. Acad. Sci., vol. 174, Art. 2, Oct. 1970, pp. 675-689.

*Primary Examiner*—Blondel Hazel
*Attorney, Agent, or Firm*—Fulwider Patton Reiber Lee & Utecht

[57] ABSTRACT

A method of preparing an autogenous vaccine for use in improving the immunocompetence of animals affected with neoplastic disease characterized by the production of choronic gonadotropin by the microorganism *Progenitor cryptocides,* ATCC 31, 874.

5 Claims, No Drawings

METHOD OF PREPARING AN AUTOGENOUS VACCINE

BACKGROUND OF THE INVENTION

This application is a continuation of U.S. Ser. No. 569,253, filed Jan. 9, 1984, now abandoned; which is a continuation of U.S. Ser. No. 171,543, filed July 23, 1980, now abandoned; which is a continuation of U.S. Ser. No. 955,878, filed Oct. 30, 1978, now abandoned; which is a continuation of U.S. Ser. No. 776,360, filed Mar. 10, 1977, now abandoned; which is a continuation of U.S. Ser. No. 672,965, filed Apr. 2, 1976, now abandoned; which is a continuation of U.S. Ser. No. 295,720, filed Oct. 6, 1972, now abandoned; which is a continuation-in-part of U.S. Ser. No. 082,806, filed Oct. 21, 1970, now abandoned; which is a continuation-in-part of U.S. Ser. No. 831,985, filed June 10, 1969, now abandoned; which is a continuation-in-part of U.S. Ser. No. 490,629 filed Sept. 27, 1965, now abandoned.

DESCRIPTION OF THE INVENTION

This invention relates to chemical substances comprising a product of the growth of a microorganism of Order II, Actinomycetales Buchanan, as identified in *Bergey's Manual of Determinative Bacteriology*, Sixth Edition, 1948, p. 111, to method of preparing same and isolation thereof and to the chemotherapeutic treatment of animals and humans therewith. Published works have identified additional species and resulted in a classification of the organism under the order Actinomycetales. This order has been reclassified as follows:

ORDER—ACTINOMYCETALES
family—Progenitoraceae
genus—Cryptocides
species—
   *Cryptocides tumefaciens*
   *Cryptocides sclerodermatis (sclerobacillus)*
   *Cryptocides wilsonii*
stains isolated from lupus erytheuratosis, rheumatoid arthritis, periarthritis, nodosum, sarcoidoses (that is, from collogen diseases other than cancer and other such diseases specified elsewhere herein)
varieties: hominis, rodentii, avii, etc. A culture of *Progenitor cryptocides* was deposited in the American Type Culture Collection, Accession Number 31,874. All of the species noted above have been observed to be interchangeable within the scope of this invention.

P. Cryptocides has been assayed and assigned the tentative formula, $C_{30}H_{38}N_2O_3$ (certain products of Cryptocides were crystals extracted from cultures of urine from terminal cancer patients). Extracts also have been crystallized from the blood and urine of cancer patients and the crystals result from the presence of the organism.

The microorganism involved (Cryptocides) has been identified as a highly pleomorphic intermittently acid-fact micro-organism, with both a virus-like and a PPLO or L transitional phase. This organism is a great simulator, whose various forms may resemble micrococci, diphtheroids, bacilli, fungi, viruses, and host-cell inclusions. Cryptocides has the ability to change its form and may vary its appearance from that of a fungus to that of a cluster of virus-size pleuro-pneumonialike organisms (PPLO or Mycoplasma). Collagenophillic mycobacterium-like, which include the cancer organism, are able to change their forms. Cryptocides has filterable or extremely small forms (submicroscopic) similar to viruses, and rather large mycelia. There were some variations as to size and some differences in the kind of media or material in which it will grow. Certain strains of it ferment one kind of sugar, some others, and some can live with little (or no) oxygen, whereas some require more. It can be identified as a single agent. The microorganism undergoes many changes in morphology and some of those forms might be zoogleal or "L" Forms. Zoogleals are intermediate forms of microorganisms which ordinarily have cell walls, but, in which, under certain circumstances the cell walls are absent. Some of these forms can be passed through very fine filters that hold back the usual bacteria and allow only very small particles such as viruses and small L forms to pass through. Such filter-passing bodies can regrow to become bacilli (bacterial cultures). The microorganisms involved have many forms but they always grow up to be the same thing no matter how often they are cultured. Cryptocides is not a virus but is a pleomorphic bacterium.

Cryptocides is acid fast, that is, it retains the Ziel-Neelsen stain in the presence of acid. Cryptocides is related to the tuberculosis family of microbes. It is filterable through filters designed to hold back bacteria. It is sensitive to tetracycline, kanamycin, ampicillin and furacin, but occasionally resistant to pencillin, sulfa drugs and mycostatin. As for the pleomorphism, cryptocides exists as virus-sized bodies of 20 to 70 microns, as elementary bodies of 0.2 micron, and in coccoidal forms of 0.5 microns or larger. The latter are usually gram-positive and resemble common micrococci but are distinguishable by variation in size and the sprouting of filaments or spicules. The organism may also appear in amorphous mycoplasmalike forms, as rods or filaments of varying lengths, and in older cultures, as spores and hyphae.

Cultures made from animal tumors and fluid have great similarities with cultures derived from many types of fresh uncontaminated human tumors, from blood and other body fluids of patients who have advanced cancer.

The L-forms are bacterial forms without cell walls. They resemble pleuro-pneumonilike organisms (PPLO), also known as mycoplasma. However, the mycoplasma appear to reproduce continously under some conditions in the same stage, with the absence of cell walls, while other organisms have a tendency to revert more quickly to the more stable bacillary or coccal forms of origin. The L-forms are the link between bacteria and the viruslike minute bodies that are a stage in the life cycle of certain microorganism. Many viruses may actually be L-forms of microbes which, under certain conditions may be induced to return to their original forms. Previously the appearance of the both adult and L-forms led to the erroneous conclusion that there was a mixture of microorganisms, a contamination of pure strains with other nonrelevant microorganisms, but this was shown to be an erroneous misconception. Some true contaminants are readily recognized by their growth pattern but the Cryptocides is a great simulator of other organisms. It requires infinite patience to observe its growth pattern and to recognize its transition from one form into another.

The microorganism involved requires definitive bacteriologic media for its primary isolation, differential staining techniques for its identification, high power microscopic resolution, and the electron microscope to reveal its most minute forms. Specific cultures can be obtained on solid media used for the isolation of the tubercle bacillus. This mycobacterium-like organism is believed to be a primary etiologic agent in proliferative and degenerative diseases such as cancer and perhaps many other socalled autoimmune diseases. Cryptocides is believed to be the causative or infectious agent (microbial) of cancer, in all of its forms, Cryptocides would therefore be called an antigen. More specifically, the filterable forms of P. Cryptocides which are of virus size are the causative agents in human and animal cancers.

Peyton Rous did not call his tumor filtrates (from chickens) viruses but instead "tumor agents." His material could be dried and held on a shelf at room temperature for months and then, mixed with saline, it could be reactivated to initiate fresh tumors. A true virus has been defined as a submicroscopic infectious unit that lives only in the presence of living cells and cannot exist even momentarily outside of them. Many have tried to find a virus implicated in some form of human cancer, but none has been found.

Applicants have grown the Rous tumor agent in sterilized beef broth that contained suitable nutrients for bacterial growth, and traced its growth pattern through all of the bacteriological stages. Applicants knew that the infectious agent passed through filters that permitted only the passage of so-called viruses. Applicants filtered the cultures, not the extracts of the tumors, through bacteria restraining filters and studied these with a electron microscope. Applicants kept the cultures in which there did not appear to be any visible form of life, incubated them at 37° C. and from these seemingly clear broths with the agent in them, there arose the bacterial and fungal stages of the cryptocides. Applicants ruled out contamination that might account for the bacterial growth on incubation by repeating the experiment dozens of times. It was a tedious process but proved that this so-called virus could and did convert to a bacterium that had not only submicroscopic forms but also bacillary, coccal or round forms, and that could also develop funguslike stages and spores. (On studying the growth of the tubercle and lepra bacilli these stages were entirely comparable with the Cryptocides.)

When applicants examined the cultures obtained from human cancers, there was no discernible difference in the growth pattern. The growth pattern of the chicken cancer isolates and that of man were the same. They grew in the same kind of broth in the same way and they appeared the same in chicken and human tissues. They had the same staining properties with the Ziehl-Neelsen dye. Applicants did sheep immunization studies in which they found significant cross-agglutination between the Rous sarcoma, fowl leukosis and various strains of human cancers. When applicants injected the isolated cultures into mice, the characteristic disease and lesions developed. The Rous isolates had to be readapted to chicken tissues by passage on the allantoic membrane of fertile eggs and then replanted into young chicks. Applicants also carried on immunization of rabbits with the leuokosis agent and used the antiserum to cure chickens dying of fowl leukosis. In every way the Rous agent appears to be a prototype for human cancer.

The above studies led to the cultivation of the same kind of microorganisms from other animal tumors. These invariably grew and appeared similar to the Rous and human strains. Sometimes there were differences in size or different sugar or oxygen requirements for cultivation, but essentially they were the same basic type or organism.

The cancer organisms (cryptocides) appear to resemble mycoplasma, organisms that exist without cell walls, expecially since the cytosinguanine ratio of their mucleic acid, DNA, is similar to that of certain mycoplasma. However, the usual mycoplasma tend to remain in their state of existence without cell wals but the Cryptocides may pass rapidly through the stage without walls to the form of true bacteria. Perhaps all mycoplasma could be induced to become bacteria but this is still a disputed point.

Dr. Robert Huebner, head of the National Institute of Allergy and Infectious Diseases, Bethesda, Md., has stated that cancer is a viral infection. Of the various agents suspected, he stated that the C-particle is the most likely agent. It has been called by this name because the round bodies found in cancerous tissues often appear in a C shape. However, the comparison of the C-particles in mouse leukemia with the filted Cryptocides isolates examined under the electron microscope show them to be similar in size and shape. In preparations from cultures the round forms are often seen to split and assume the C form. It would seem that this splitting into a C is characteristic, but not necessarily a method of identification. All the other methods are necessary as well.

The cancerous growth itself is not the entire disease. The small coccuslike granules which can be seen dividing in cancer cells represent the intracellular parasite that is the causative agent. The parasite within the cancer transforms the normal cell into a sick cell that cannot mature by differentiation. It is the filtered material from tumors and other cancerous growths, as well as the cells themselves, which transmit cancer from one species to another species. Or, in other words, the cancerous agent can cross species barriers and infect other species.

P. Cryptocides not only causes cancer but a number of other ailments that effect man. The infectious nature of arthritis, of some kinds of heart, liver and kidney impairment, and most recently of diabetes is known. The patterns of these diseases point to their latent infectious nature. Cryptocides is an infectious agent. But, the tumors are only a part of the resultant disease. In addition to tumors, there are cheesy lesions or areas resembling tuberculosis, which can involve any one of the essential organs such as the liver, kidney heart or lung. These organs might show changes in the connective tissue, called collagen, which can lead to degeneration as seen in the chronic human degenerative diseases. The organism may assume a latent form and be inactive as long as the body's defense mechanisms are adequate, but when they are not, disease results. The exact kind of disease depends on the age of the host and its state of resistance, as well as the strain of the organism.

All cancerous bloods examined have revealed the cryptocides organisms. Applicants have made a film of untreated blood from a terminal cancer patient in which the parasites are seen in Brownian motion in the red cells. The parasites stay inside the cells of patients who are holding their own against the disease, but in advanced cases, the numerous cells rupture, releasing the organisms.

The microorganism is apparently ubiquitous in nature, existing in a reservoir in soil and water, and is found in all classes of animals, including man. It can exist as a latent infection in host tissue without causing apparent ill effects. However, when the immunologic barriers are lowered it can invade the host in prodigious numbers and involve any or all of the host tissues, causing various kinds and degrees of pathologic change equilibrated between the ferocity and numbers of the invader and the ability of the host to resist them. Not only is the organism pleomorphic but the pathologic changes induced in experimental animals show varying degrees of disease ranging from the lethal through the semi-immune, neoplastic and degenerative stages. Hyper-immune and degenerative stages may be relatively quiescent but can become slowly and progressively fatal.

Man and/or animal can be a latent carrier of the Cryptocides. Many of applicants' experimental animals that have surived cancer have developed interstitial collagen disease as a result of their inoculations with applicants' bacterial isolates of Cryptocides, and also developed heart lesions. When baby mice born of infected mothers died, the autopsy showed destruction of heart muscle. These lesions contained the acid-fast organisms (Cryptocides) in the heart muscle. Also, a number of research people in England have reported strange microbic bodies previously unrecognized in the hearts of people who died of coronary disease. One of the applicants had cancer of the forehead treated successfully with radium fifteen years previously, but was a latent carrier of the Cryptocides. That applicant was treated after that period of time with an autogenous vaccine, has had a new vaccine prepared every year, and has continued treatment.

"Mycobacterial Forms in Myocardial Vascular Disease", Virginia Wuerthele-Caspe Livingston and Eleanor Alexander-Jackson, (1965) proposes the theory that there are microbic bodies in the lesions of heart diseases and that they are especially numerous in the areas where the blood vessels have ruptured. Until recently the theory has been the coronary blood vessels of the heart are narrowed due to arteriosclerosis, and that fatty deposit in the wall of the vessels, and overweight are the determining factors in this type of heart disease. Now the medical researchers are becoming aware of the fact that the blood bessels themselves are often not involved so much as the supporting tissues and muscles of the heart so that the heart vessels rupture due to extrinsic factors outside the vessel rather than from intrinsic disease. This is particularily true of patients with collagen diseases such as scleroderma and lupus erythematosis. Vascular and myocardial pathology is related to chronic low-grade infection by the mycobacterium-like organisms (Cryptocides).

Degenerative changes occur in coronary heart disease in the presence of the invasive mycobacterial parasite cryptocides.

Postmorten heart sections of 6 patients with coronary and aortic disease were stained by the Fite modification of the Ziehl-Neelsen technique (for demonstrating Lepra bacilli in sections) using Kinyoun's carbon-fuchsin, and compared with sections of the same involved areas stained with conventional H and E. Eight predominant types of lesions were observed in the myocardium 1. PERIVASCULAR CHANGES AROUND THE SMALL CORONARY VESSELS. In the loose connective tissues numerous small acid-fast bodies can be seen.

2. CELLULAR INFILTRATION. This is frequently seen not only around the vessels but between the muscle fibers as well. These cells consists almost entirely of mononuclear types, predominantly lymphocytes, while large mononuclear phagocytes laden with organisms plasma and other mononuclear cells are present in relatively large number.

3. FIBROBLASTIC INFILTRATION. The presence of these organisms appears to stimulate the formation of fibroblasts. In some areas, the muscle fibers and interstitial tissues appear to be replaced by fibroblasts.

4. INFARCTION. Where there has been an infarct, there may be a softened central area with numerous small acid-fast cocci and coccobacilli present in the collagenous hemorrhagic softened area. 5. NECROSIS. Necrotic changes may involve the blood vessels. Striking degenerative changes of the vessel walls are observed as illustrated not only by the sections of coronary vessels but also by the sections of in involved aorta. Proliferative changes may involve the endothelium, with invasion of the endothelial cells, and are accompanied by thickening and narrowing of the wall. Hairlike filaments of the organisms were seen protruding into the lumen. These changes are also present in the vasa vasorum of the aorta.

6. THROMBOSIS AND RECANALIZATION. Some areas of recanalization were observed in heart, liver, and spleen.

7. CHANGES IN THE ELASTIC LAYER OF THE AORTA. The elastic fibrils have lost their identity and have become collagenized with loss of structure. As scar tissue forms, cholesterol-like plaques occur. It seems possible that deposity may be derived in part from the fatty envelopes of these organisms. In other tissue where masses of the organisms have proliferated, polyhedral crystals resembling cholesterol have been observed.

8. CHANGES IN THE HEART MUSCLE. Individual nuclei of the heart muscle are frequently parasitized, and replaced by small acid-fast globoidal bodies. The muscle fibers themselves appear in a state of gradual digestion and disintegration by both minute and larger acid-fast forms.

All of the above can be treated and detected by this invention

Neoplastic changes have been shown by Diller and Diller (*Intracellular acid-fast organisms isolated from malignant tissues*, Trans. Amer. Micr. Soc., 84:138–148, 1965), to arise in tissue culture as the result of exposure to this specific invading microorganism.

The *Journal of the American Medical Association*, July 28, 1969 Vol. 209, No. 4, contains a summary of the work of K. A. Bisset, *New Scientist*, June 12, 1969, who speculates that many diseases like leukemia and arthritis could be caused by Mycoplasma or by forms of this elusive bacteria and wrote that the fact that mycoplasm can break down into viruslike particles, easily identifiable on electron-microscope examination and similar to those found in blood of leukemia patients, leads to a strong suspicion that Mycoplasma may be a culprit in the development of certain malignant processes.

Dr. Florence B. Seibert, Veterans Administration Research Laboratory at Bay Pines, Fla., has reported immunologic studies with the organisms. Labeled antiglobulin, which was specific for an isolate from a human breast, adenocarcinoma induced specific fluorescence in the white blood cells of patients with leukemia and myeloma, demonstrating an immunologic relationship.

Koch's law is the foolproof method of proving the cause of a disease. It is as follows:

1. The microorganism must be present in every case of the disease.
2. It must be possible to cultivate the microorganism outside the host in some artifical media.
3. The inoculation of this culture must produce the disease in a susceptible animal.
4. The microorganism must then be reobtained from these inoculated animals and cultured again.

Applicants have fulfilled Koch's law using pure, uncontaminated cultures of cryptocides. Pure cultures were obtained repeatedly from the various proliferative and neoplastic diseases of both men and animals. Then they were injected into animals capable of being infected. Gradually diseased areas developed which resembled those from which the cultures were obtained. Then the pure cultures were reisolated from the infected animals. Thus Koch's postulates were fulfilled.

A blood specimen of a terminal cancer patient was cultured, the culture was extracted and the extract produced tumors in mice. This demonstrates the growth factors.

In one attempt to produce antibodies and antiserum in sheep that would be beneficial in the treatment of human cancer, sheep were immunized with an attenuated or weakened culture. Twenty sheep were examined and found to be free of disease. Some of the stock cultures applicants had on hand such as cultures from human breast cancer, from a sarcoma of a young boy, from a human leukemia, from the Rous chicken tumor, from arthritis, and from fowl leukosis, were attenuated. Applicants injected two sheep with each strain. After about four weeks, some of the sheep became sick. Attenuated vaccines from the cancer cultures were used weekly for immunization. Several ewes aborted their young. The fetuses were macerated. Some of the sheep developed very swollen painful joints and could scarcely graze. Others looked poorly because emaciated. Applicants realized that the vaccines which were attenuated were still alive and had not fully immunized the sheep but had diseased them. The sheep were bled in order to assay their serum for antibodies. Sera was obtained but the sheep had to be destroyed. Although the sheep had to be destroyed applicants learned that the fowl leukosis serum agglutinated in high dilution the cultures from the boy's sarcoma, that the breast cancer serum reacted with the human leukemia isolates, and that the Rous sarcoma serum reacted with all of the cultures. This meant that the cultures from the human cross-reacted with one another strongly and with the animal sera, showing that tumors are not tissue or species specific.

Three chickens having fowl leukosos, a cancerous disease, and which could no longer stand up, were taken to applicants' laboratory and in a short time they were dead. Applicants made cultures from their heart's blood. These grew to be the same kind of cultures as those derived from all of the other tumors experimented with by the applicants.

A pure, selectively grown bacterial culture of the type described above, obtained from urine and blood using sterile precautions, contains chemical substances related and/or identical to the actinomycin group. To test this point, a phenolized pure culture was acidified with HCl to pH 2 (Congo red/thymol blue) and was left standing overnight after short boiling. A mixture of n-butanol/conc. NaCl, equal parts by volume, containing a few drops of glacial acetic acid, was used for extraction. After gentle shaking for about 15 minutes a dark cherry-red layer of the solvent was separated for further processing. This crude mixture gave peak absorption at 440/450 mn and 410/425 mn values which compare favorably except for a third absorption peak at 240 m$\mu$ obtained by Waksman (Waksman, S. A., and Lechevalier, H. A.: The Actinomycetes, vol. III, The Williams & Wilkins Co., Baltimore, 1962, p. 168) which was missing. From an ascending paper chromatogram a reddish zone was eluted with ethylacetate and an acetone-ether mixture, both gave upon evaporation some microscopic crystals (red plates). The controls containing broth and 2% phenol but no organism gave upon extraction a barely yellow-tinted layer of the solvent. This exploratory separation technique was then repeated with several 25-hour urine specimens obtained from terminal cancer patients. After separation of the organic layer from the urine specimens again a more or less pronounced color was present ranging from dark honey-brown to cherry red; controls taken from healthy persons did not contain such colors. The presence of these dark colored compounds seems to be most pronounced in terminal cases. All crude mixtures isolated from cultures and/or urine were subjected to further separation by chromatographic techniques.

METHODS FOR THE ISOLATION AND IDENTIFICATION OF A PLEOMORPHIC INTERMITTENTLY ACID-FAST ORGANISM FROM NEOPLASTIC DISEASES, AND THE PREPARATION OF CULTURES

Isolation from Urine (Crofton Method)

Obtain a midstream clean-catch specimen of urine in a sterlized screw-top glass container.

Make up DiFco's brain-heart infusion agar: 37 grams of the agar base are added to a liter of distilled water, heated to melt and mix, and distributed into flasks or bottles of 95 ml amounts, and autoclaved. Five percent (5%) human blood (outdated bloodbank blood may be used) is added when the melted agar has cooled down to 45–50 degrees C., and the mixture is poured into sterile Petri dishes.

Streak the surface of the blood agar plate with a sterile swab which has been dipped in the urine. Incubate plate to 37 degrees C. and examine after 24 hours. If growth has appeared, note types of colonies, make duplicate smears, and stain one by Gram's stain and the other by Alexander-Jackson's modified Ziehl-Neelsen technique: flood side with Kinyoun's carbolfuchsin for 3 to 5 minutes in the cold, wash, decolorize briefly with 70% alcohol containing 1 to 3% HCl as these organisms decolorize more readily that M. tuberculosis, counter stain by flooding slide with Loeffler's methylene blue and add 6 to 8 drops of normal (4%) sodium hydroxide. Tilt slide to mix, and wash after 30 seconds.

APPEARANCE OF THE MICROORGANISMS ON BLOOD AGAR

Colonies—usual types of growth obtained 1. white discoidal, often hemolytic, and with a raised center—having a fried egg appearance, but usually larger than classic PPLO colonies grown on PPLO agar.
2. grayish muccoid, often confluent.
3. pigmented: yellowish, occasionally pinkish coral.
4. wrinkled intermediate SR worm-casting type resembling M. tuberculosis colony.
5. dull granular surfaced, irregular edges, often hemolytic, and resembling B. subtilis, but virulent for mice.

Motile forms transferred tp A-J broth produce a white or grayish white soft rim or pellicle, and a toxin-like substance.

This organism tends to resist emulsification to some degree when a loop of culture is rubbed with a drop of water on a glass slide to make a smear.

MICROSCOPIC APPEARANCE

The cancer isolate is either Gram positive or Gram variable. The Gram stain is not the stain of choice, but should be used to eliminate true Gram negative organisms, which show no Gram positivity at all such as B. coli, proteus or pseudomonas.

Acid-fast forms may or may not be found, as this organism is intermittently acid-fast rather than more consistently so as in M. tuberculosis or other classic mycobacteria. However, if possible, careful search for acid-fast forms is desirable, as they are hallmarks of this mycobacterium-like organism. Slender filaments, sometimes with lateral branching, and sometimes acid-fast, help to distinguish it from common micrococci. The rods may be slender and diphtheroidal, or thicker and subtillis-like. The latter sometimes contain tiny brightly acid-fast bodies surrounded by a colorless vacuole-like area or capsule. This appearance plus virulence for mice and guinea-pigs distinguish them from subtillis rods. The main morphologic forms are:

1. tiny acid-fast elementary-type bodies, often refractile;
2. Coccoidal forms of varying sizes with or without threads or protruding filaments;
3. rods as described above; X, Y, and V forms commonly seen, filaments may become very long and wide;
4. cyst-like bodies of various sizes from 3 to more than $10\mu$ and often containing smaller bodies which may be brightly acid-fast;
5. L or PPLO forms consisting of a lightly stained matrix containing more deeply stained bodies of various sizes, or tangled branching threads and ring-forms. These are revealed by Alexander-Jackson's Triple Stain modification of the Ziehl-Neelsen technique;
6. spore forms of oval shape seen in old cultures;
7. sub-microscopic bodies 20–70 $m\mu$ revealed by the electron microscope, and of virus size.

The product of the growth of the specific Actinomycetales organism is a chemical substance which is obtainable on recrystallization (Wolter)—of a suspension of the isolate with conventional paper chromatography annular separation procedures, and identifiable as comprising a formation of (a) red crystals identical with those described by Waksman as having the absorption peaks indicated, supra;

(b) yellow crystals, similar to an actinomycin D fraction;

(c) formation of small placques of crystals similar in appearance to gramicidin;

(d) a waxy, higher-alcohol formation, and (e) a brownish, foul aromatic residue.

CHROMATOGRAPHIC IDENTIFICATION

To an acidfied (pH 5) sample of urine in which the organisms are grown, (phase I) and kept in the refrigerator, is added one-fourth volume of n-butyl alcohol and the mixture is shaken for one-half hour. The mixture is refrigerated until the layers separate. Separation is done by decantation first and then by using a separatory funnel. The butanol layer has attained a reddish brown color and in some cases a yellowish color. This procedure results in an aqueous phase (II) and a butanol phase (III). The aqueous phase is extracted once or twice more in the same manner with n-butanol, so long as the color appears in the extract.

A portion of the combined extracts is evaporated in an evaporator at 35°–40° C. The dried residue is dissolved in a small amount of methyl alcohol, solution (IV). Layers of a silica gel preparation, MM-SGel-HR for thin layer chromatography, Machorey Nagel and Co. 516 Durem, Germany, is spread on glass plated, prepared, dried and stored in a dessicator. By means of a small pipette, a spot of solution (IV) is placed on the silica gel layer of one of these plates near one edge and near this spot at the same distance from this edge and in the same way, another spot of actinomycin D, (Merck, Sharp and Dohme), is placed in the same manner. Both spots appeared bright yellow. Other pairs of spots of these two solutions are placed on the same row using 5 $m\mu$, 10 $m\mu$ and 15 $m\mu$. (One $m\mu$ equals one microliter.) Of the solvents tried for developing the chromatograph, the most effective was butanol-methanol-water in the ratios of volume of 6:1:3. 60 ml. of butanol, 10 ml methanol and 30 ml of distilled water are mixed and put into a thin layer chromatography chamber. The paper lining the walls of the chamber is wet by swirling the solution in the chamber. Then the plate with the spots is placed on edge in the chamber with the row of spots parallel to and near the bottom but above the surface of the solution. A cover is placed over the top of the chamber sealing it. The chamber is kept in the dark during the process of separation since a better yield elution is obtained. In previous runs each actinomycin D spot travelled as a single spot leaving nothing in the pathway by visible or ultraviolet light, and phase (III) left material spread from the top streaking down along the pathways. However the top was always at a level with and the same color as the actinomycin D. Subsequently, after drying the plates, the actinomycin D spots and those portions from the spots of phase (III) on a level with the actinomycin D spots are cut out and separately eluted with methanol, as are other portions from the spots of phase (III), since these may contain other actinomycins than actinomycin D. Visible ultraviolet and infrared absorption spectrograms are made of the different elutes and compared. The TLC method is based and adapted from methods reported by Cassani et al, J. Chrom. v. 13, 1964, 238–239.

ACTINOMYCIN BIO-ASSAY

Blood and tissue cultures and urine samples obtained in accordance with the foregoing procedures were extracted with and equal volume of butanol, water, acetic acid (4:5:1) and the upper phase taken to dryness. The residues were taken up into two 5 ml. portions of ether and evaporated at 35°–40° C. Paper discs were dipped into ether solutions of extract, the ether evaporated and the discs placed on standard actinomycin assay plates. A standard preparation of actinomycin D was also run. The zones of inhibition are shown in Table I; zones above 15 mm. in diameter fall within the standard range and are calculated in terms of actinomycin D equivalent.

TABLE I

| | Zone Diameter (mins). | Act. D (ug/ml) |
|---|---|---|
| Broth Extracts | | |

TABLE I-continued

| | Zone Diameter (mins). | Act. D (ug/ml) |
|---|---|---|
| (1) | 14 | <0.2 |
| (2) | 15 | 0.2 |
| (3) | 16 | 0.4 |
| (4) | 12 | <0.2 |
| (5) | 16 | <0.4 |
| (6) | 14.5 | <0.2 |
| (7) | NA | <0.2 |
| (8) | NA | <0.2 |
| (9) | 14 | <0.2 |
| (10) | NA | <0.2 |
| (11) | NA | <0.2 |
| (12) | NA | <0.2 |
| (13) | NA | <0.2 |
| (14) | NA | <0.2 |
| (16) | NA | <0.2 |
| Urine Extracts | | |
| (15) | NA | <0.2 |
| (17) | 22 | 4.2 |
| (18) | 16 | 0.35 |
| (19) | NA | <0.2 |
| (20) | 18 | 0.8 |
| (21) | 17 | 0.5 |
| (22) | 13 | <0.2 |
| (23) | NA | <0.2 |

UV ABSORPTION CURVES 0.2 ml. of each ether solution was evaporated to dryness and the residue taken up in 1 ml. of methanol and UV absorption curves were recorded. End absorption at this level of purity prevented measurement of 440 mm. absorption. Small peaks, typical of trace amounts of actinomycin, were found with samples 1-6 inclusive and sample 8 with a slight response present with sample 17. Definitive biochemical tests such as the cytosine-guanine percentage of the DNA have helped to classify the cryptocides microbial isolates.

Further concerning cryptocides, these organisms, which appear primarily as small acid-fast granules in young cultures, and which tend to become non-acid-fast in the larger forms present in older cultures, may exhibit a number of morphologic phases with intermediate transitional forms. These include (1) filterable and submicroscopic bodies; (2) larger granules readily visible under the light microscope an often resembling ordinary micrococci; (3) larger globidal cystlike bodies and thin-walled sacs containing the smaller forms; (4) PPLO or L type zoogleal symplasms without cell walls; (5) rods of various sizes capable of developing a characteristic motility; (6) long filaments and threads which may show lateral branching; and (7) thick-walled spore-like bodies. The lesions produced by these organisms in experimental animals were generally pseudocaseous, degenerative in type, occasionally neoplastic, and occurred principally in the liver, kidneys, and lungs although at times, there was involvement of the heart, spleen adrenal glands, stomach, lymph nodes, and omentum.

Dr. Afton Munk Livingston, and Dr. Virginia Livingston, Transactions of the New York Academy of Sciences, May 1972, report the recognition of the P. cryptocides organisms in the blood of cancer patients compared with the blood of healthy individuals, of which a summary follows. Examinations by darkfield microscope of fresh blood, and also by brightfield microscope using supravital stains serving as a diagnostic and prognostic tool in following the course of the cancerous disease in the patient in conjunction with several other microbiological evaluations.

PREPARATION OF SLIDES FOR BLOOD EXAMINATION

The patient's finger is immersed in 70 percent alcohol and air dried. A steril lancet is used to puncture the finger, a small drop of free-flowing blood is placed on a sterile clean slide and covered with a sterile covership. Care is taken that the blood does not flow beyond the edge of the coverslip. Using a small weight for approximately one minute, light pressure is applied to the coverslip to spread and separate the blood cells. The preparation is then examined under darkfield at $\times 750$ and $\times 1350$ magnification. For lightfield examination, the same method is followed and in addition, a small drop of 1 percent aqueous sterile crystal violet, freshly prepared and filtered, gently applied to the preparation. If the number of organisms, to the blood as well as the motility of the various stages are to be evaluted, then the blood is diluted 1:100 with sterile distilled water using a sterile red-blood-cell diluting pipette. The pipette is then thoroughly shaken and a few drops are expelled from the pipette into a sterile Petri dish. A small measured amount of 1 percent aqueous crystal violet is added. This mixture may then be used to flood a blood counting chamber. This method provides a quantitative estimate of the numbers of the organism as well as their motility, which may last as long as fifteen minutes. However, for the usual brightfield examination of the blood with crystal violet, the blood drop is placed directly by the slide and the small amounts of crystal violet is added before the coverslip is placed over the preparation and light pressure applied.

DARKFIELD EXAMINATION OF UNSTAINED FRESH BLOOD PREPARATION

A number of interesting observations may now be made by the darkfield, pulsating orange bodies in the red cells may be observed. In the background, there are bright dancing forms which appear to be small L-forms of the organism. In several infected hosts a number of motile rods may be observed. Spheroplasts and mesosomes both large and small are present. These may have many fine delicate vibrating forms in their periphery. Forms resembling a medusa or a octopus with waving filaments may be present. Organisms may bud from the surface of the red cells and from fine hairlike filaments which resemble the handle of a tennis racquet. There may also be numerous threadlike filaments free in the serum, varying in size, some 10-15 microns in length. These are motile and appear to wind in and out around the red cells. There are also long tubular structures 50 microns or more in length, and about 10 microns in width that are milky white, highly luminescent, containing numerous refractile granules. The tube in some cases appears to arise from a coalescence of the L-forms or to bud from a spheroplast. It is transparent since cells can be seen through it. When the tube wall disintegrates the refractile bodies are released in the serum and may enter fresh red cells. There are also large round milky white forms appearing to be protoplasts about 20 to 60 microns in diameter which contain granules resembling spheroplasts or mesosomes. The protoplasts may have budding forms at the periphery and may release rather large vesicular refractile bodies resembling the spheroplasts or mesosomes. At times, the extruded mesosomes are large enough to be mistaken for red blood cells, but they do not have the bluish tinge of red cells seen in darkfield. Rather, minute dancing particles may later appear within them.

In addition, shrunked red cells with a ground-glass appearance spiculated at the periphery may be observed. We have termed these structures "spent cells" since they appear to be red cells that have been consumed by the parasites. They are lighter and smaller than normal erythocytes and have a tendency to be pushed to the periphery of the blood drop when it is prepared for examination. Changes in the character of the leukocytes are also apparent. Many leukocytes in the advanced stages of diseases appear smudged, inactive and only dimly luminescent whereas normal leukocytes have vigorously active granules and active amoeboid movements. Under some circumstances great numbers of fine spicules occur in the dark field. These are very delicate and appear to arise from minute L-forms. They are not thrombocytes. At times they appear to shed from the surface of the protoplasts. Why they should be more numerous at one time than at another is not understood but their appearance may be related to the pH of the blood. Orange crystalline forms of the organisms as well as free crystals may also be seen in and around the microbial clusters in the plasma. They apparently arise from the waxy-secretions of these mycobacteriumlike organisms. These are the crystals that have been extracted from pure cultures and urines of terminal cancer patients and that have been used for various types of bioassay.

BRIGHTFIELD EXAMINATION OF SUPRAVITALLY STAINED FRESH BLOOD PREPARATIONS

On a blood preparation stained with crystal violet and examined by the brightfield method a clear white light and a magnification of at least $\times 1000$ microbial forms are revealed that are not seen in the darkfield. There are large branching fungal forms that are not luminescent in the darkfield. These fungal forms may extend over a considerable area involving several microscopic fields. Some of these are branching and appear to have conidial or frutting bodies attached to their branches. Microcolonies may be clearly seen surrounding individual red cells and some appear to arise from parasites extruded from the cells. These microcolonies appear to develop into a network of interlacing branching fungal filaments which act as bridges between the red cells and cause them to adhere in clumps. The number of fungal forms which hold the erythrocytes together or adhere to their surfaces may be directly related to the sedimentation rate. The greater the adherence of the erythrocytes due to the mycelial forms, the more rapid the sedimentation rate. The red cells become separate and free as the number of both intra-and extracellular parasites diminish. The stained preparations in the counting chamber have L-forms, which appear much more numerous than in the darkfield, and occur in clusters, which have marked Brownian movement. These clusters agglutinate and become motionless after ten to fifteen minutes. Introduction of gamma globulin or specific antiserum under the coverslip of the counting chamber caused instant agglutination and cessation of motion. By this method, antibody activity of blood serum can be roughly estimated. Other dyed microbial forms in the brightfield may be compared with those in the darkfield. The vibrating orange bodies in erythrocytes in the darkfield appear as violet bodies in lightfield. The brightly luminous tubes take on a light violet color with deep purple granules.

The same comparison between darkfield and stained brightfield preparations may be drawn by examining blood cultures grown in broth. Hanging drops of cultures sealed with sterile vaseline are preferable to ordinary wet perparations since they are safer to handle and can be preserved for a longer period of time. Conventional staining of slide preparations appears to break up many of the delicate microcolonies and interlacing fungal forms. Wet supravitally stained preparations in hanging drops also indicate the degree of motility of many of the microorganisms. Other dyes have been used which penetrate to some extent but do not provide sufficient contrast. They are Sudan black, saffron yellow, Congo red, May Grunwald, toluidine blue, gentian violet, as well as several others.

All cancerous patients yielded L-forms as well as other pleomorphic stages on blood culture which, on further cultivation, developed the typical acid-fastness of the Progenitor cryptocides group as previously described. However, the cancer patient even in the advanced stages of the disease is usually afebrile. Comparable numbers of microorganisms other than the *Progenitor cryptocides* groups might be expected to produce an acute febrile reaction. There undoubtedly can be a mild or transitory bacteremia in blood due to relatively non-pathogenic bacteria such as some of the diphtheroids. However, with the previously described methods, the great numbers of the Progenitor group as a silent but lethal bloodstream infection may be readily demonstrated. Advancing infection of the bloodstream with P. cryptocides is relatively asymptomatic until large numbers of the organisms are present and there is a concomitant breakdown of the immunological and dextoxifying system.

The autogeneous vaccine is known to exist by disc-saturated inhibition on culture plates of extracts and also from the serum of cancer patients.

Administration of the autogenous vaccine should be initiated by high dilutions of the lowest order of dosage at twice weekly intervals, with gradually increasing dosages until overdosage symptoms occur. Preferably, subcutaneous injection of the autogenous vaccine in a suitable pharmaceutical carrier, such as sterile water or saline solution may be employed, although oral administration of the product in a suitable carrier also may be employed.

Use of the autogenous vaccine of this invention may prove to be of value in the palliative treatment of animals and humans afflicted with various forms of neoplastic diseases, as indicated by treatment thereof with autogeneous vaccines made from a suspension of the isolates in 2% phenol. In preparation, the vaccine is allowed to stand overnight at room temperatures, centrifuged and further diluted with 0.5 phenol or saline.

Subcutaneous injection is initiated with the highest dilution of 1 million organisms per ml and 0.1 ml twice weekly, until overdosage symptoms occur. Therapy is continued with higher concentrations, e.g., 10 million and 100 million organisms/ml. Oral administration of the same dosage can also be employed.

A study of one hundred random blood samples, taken in the office of a physician who specialized in allergy and immunologic disease, showed that all tumor-bearing patients, in comparison to office personnel used as controls, gave positive cultures for the cryptocides organism. A number of patients with chronic degenerative disease were also positive. While many patients who had reached a healthy old age were negative, several "tired" young people without apparent disease were positive.

A reddish brown material has been extracted from the tissue, urine and blood of cancer patients in increasing amounts as they became terminally ill, and (this material has not been found in normal controls. It is carcinogenic for mice, increasing the incidence of pulmonary tumors. The biological effects have been assayed in preliminary studies with tissue-culture systems and with tumor-genesis in mice.

The applicants have found the presence of actinomycin-like crystals in body tissues and in cultures.

The basic requirement for formation of the cancer cell is the causative microorganism; all other factors such as coal-tar irritants, other microorganisms, the aging process, any chronic irritants leading to poor local resistance and giving rise to immature, succeptible reparative cells, may prepare the living matter, e.g., for the multiplication of the cancer organism and its penetration into the cyptoplasm and nucleus of the host cell.

Apparently the organism cryptocides can invade both cytoplasm and nucleus of host cells in any type of host tissue when body defenses are lowered. In experimental animals it can cause lesions that appear as necrotic abscesses, granulomas, fluid-filled cysts of neoplasms. The type of lesion apparently depends on specific and nonspecific immunocompetence and the age of the host.

Certain chemicals can have a tremendous effect upon the entire hormonal system. One of these substances is actinomycin produced by several of the actinomyces organisms and probably by many of the Actinomycetales. There is a whole array of chemicals and biologic produced by this group of microbes, which have been used as antibiotics and antineoplastic agents in some cases. The actinomycins even in very high dilution of one part in a billion or more may have a profound effect upon the entire business of life. The important thing to remember is that no funtcion of the body is exempt from this toxic material which is produced by these microorganisms belonging to the Actinomycetales. Not only are the normal functions of the host's hormonal system deranged but there are "false or counterfeit hormones" produced with further throw the body off balance. There is a practice of castrating men and women to arrest the growth of cancer. If castration is successful in prolonging life, then adrenalectomy and pituary gland removal might be done when the effects of tumor inhibition from the castration have worn off. This hormonal ablation presents a grim picture to say the least. Applicants believe that the hormonal stimulation of the sex glands, the adrenals and the pituitary are the result of toxic materials, hormonal derangers and counterfeit hormones, such as, phytosterols produced by the Cyptocides, that upset the balance of the patient's hormones not only by inhibitory effects by production of pseudo or counterfeit hormones that act on the physiologically controlled, normal glands causing abnormal response. Also various kinds of cell poisons and inhibitors destroy the efficacy of the lymphocytes to attack the cancer cells. The cancer cells themselves are prevented from reaching maturation by these cell poisons They are sick cells unable to reach a normal maturity and normal function, whereever they are located and whatever tissue they may be whether glandular, interstital, bone or blood.

The most important thing is to try to destroy the microbes that were producing the aberrant cell inhibitors and false hormones. However, it has been reported that low testosterone levels have been induced in patients with cancer of the prostate by treatment with diethylstilbestrol, a synthetic hormone; and aminoglutethimide, a powerful inhibitor of adrenal corticosteroid biosynthesis, with patient improvement. Furthermore, an immunological mechanism appears to be involved; the inhibition of steroid biosynthesis. By removing the lympholytic effect of corticosteroids, there is produced a marked hyperplasia and increase in the number of circulating lymphocytes which potentiate the immune response. The presence of lymphocytotoxic antibodies has been reported in patients with prostatic cancer. Perhaps this steroid is a "false steroid" and antagonism by the amino-glutethimidine and diethylstilbestrol may permit an increase in the production and circulation of normal lymphocytes capable of attacking the cancer cells.

The role of steroids in chronic diseases was demonstrated by Edward Kendall and Philipp Hench in their studies in rheumatology for which they received the Nobel Prize in 1950. It is true that the steroids do not have an inhibitory effect on these diseases but at the expense of suppressing immunity and permitting the underlying latent infection to continue or to increase in its growth potential.

It is known that a bacterium belonging to the Actinomycetales was able to produce unlimited amounts of steroids from the Mexican yam.

It is stated that some steroids decrease the numbers of circulating lymphocytes as well as blocking immunocompetence. Perhaps the "false steroids" are really responsible for this action. It has been shown that certain toxic antigens prevent the lymphocyte from maturing and become immunocompetent. Leukemia, or an accumulation of large numbers of cells, either lymphocytes or polymorphonuclear leukocytes, may represent a blocking of the pathway to maturity by a toxic agent such as a steroidal or actinomycinlike compound produced by the cryptocides. Perhaps the blocking factor may be related to a protective mechanism directed toward making the cryptocides insusceptible through some biochemical fraction that blocks the immune reaction of the lymphocyte.

The present invention is useful in the treatment of man and/or animal. Safety and effectiveness of the present invention has been demonstrated in animals and has been indicated in the treatment of humans by administration of the aforesaid vaccine form.

Among the various neoplastic diseases (often termed diseases of unknown etiology) subject to palliative treatment are cancer, tumor of the lymphoid tissues, Hodgkin's disease, reticulo-endothelial tissues, arthritis, lymphosarcoma, the broad spectrum of epidermoid cancer, scleroderma, adenocarcinoma, fibrosarcoma, liposarcoma, myosarcoma, acute glomerulonephritis, leimoya sarcoma, osteogenic sarcoma, chondro sarcoma, myeloma, rous chicken sarcoma, coal-tar-induced cancer, fowl leukosis, animal tumors such as Rous, Walker, Sprague-Dawley, Shope and Sarcoma 180, and the like. Many of the foregoing are degenerative and antoimmune diseases.

Malignancy is a neoplastic infection, which depends on the number and virulence of the invading organism, the susceptibility of various organs to it, as well as the natural immunologic components of the host.

The reddish-brown crystalline substances extracted from broths containing organisms within this invention are antibiotic to the bacteria and to all strains of the producing organisms themselves.

MEDIA

The preferred media for growing cryptocides are obtained with Alexander-Jackson's broth, and with Wuerthele-Caspe's autoclaved chick embryo agar. The method of preparation of these two media is given below.

ALEXANDER-JACKSON'S (A-J) SENSITIVE PEPTONE BROTH

Ingredients:

| | |
|---|---|
| water (distilled) | 2,000 ml |
| beef lung, cut up | 2 pounds |
| peptones | 20 grams; 5 grams of each of (a) myosate, (b) gelysate, (c) trypticase, (d) phytone |
| glucose | 10 grams |
| glycerol | 80 ml |

Boil the beef lung and water for 30 minutes. Filter through cotton or very coarse paper into a flask containing the other ingredients, and heat to dissolve. This crude lung broth can be autoclaved and stored in the icebox, and clarified subsequently. Autoclaving for a second time does not seem to produce any adverse effects.

Clarification:

A 1 to 2 mm layer of infusorial earth (Standard Filter Cel of Johns-Manville Co.) is deposited on a No. 42 Whatman paper disc by laying the disc on a Buchner funnel, applying suction, and then carefully pouring on about 500 ml of a 5 percent suspension of Filter Cel. After the deposition of the layer, when the water goes through clear, the suction flask is well rinsed out. The hot medium can now be filtered through the prepared disc into the flask.

The medium should be filtered a second time through a Buchner-type funnel with a fine fritted glass disc, or else passed once more through the same Filter Cel.

pH adjustment:

The pH of the medium should be adjusted to 7.4 with sodium hydroxide. The medium is then tubed into screw-top glass tubes 150×25 mm (Kimble Glass Co., Toledo, Ohio). The tops of the tubes are not screwed tightly until after autoclaving. Autoclave for 15 minutes at 15 pounds pressure. Place about 5 ml of medium into each tube; or place 50 ml in a 250-ml Erlenmeyer flask for primary isolates. Close the flasks with cotton plugs held in a single layer of gauze, and protect the plug by a paper drinking cup or cone.

The A-J broth is obtainable from the Colorado Serum Company of Denver, Colo.

Whole fresh citrated or untreated blood, 0.2 ml is added to 2 ml of broth at pH 7.4, and incubated for a week. A transfer to fresh broth is then made to rid the culture of antibodies or other inhibitory substances. After several days, the organisms appear as a mat at the bottom of the tube. When motile rod forms are present, a soft while ring or pellicle appears. Growth is often seen climbing up the side of the glass tube.

The peptones included in the above broth have been studied individually. Myosate, a pancreatic hydrolysate of heart muscle, favors small virus-like and coccoidal forms. Gelysate, a gelatin hydrolysate, appears to favor slender acid-fast rods and non-acid-fast rods containing acid-fast granules. Phytone a papaic digest of soya meal, and trypticase, a pancreatic digest of casein, both favor the readily growing motile rods. A combination of all four peptones provides a medium which allows a wide variety of forms to develop, and makes it easier to recognize the presence of the organism in primary isolations.

WUERTHELE-CASPE'S CHICK EMBRYO AGAR

The contents of 8-15 days old embryonated hens' eggs are ground up on a Waring blendor, mixed with 1.5 percent melted agar, tubed in screw-top glass tubes, preferably large ones, slanted, an autoclaved at 15 pound for 20 minutes in the slanted position.

Examples of other media which can be used are Difco's brain-heart broth with and without glycerin, Dubos medium, Alexander-Jackson's modification of von Szabocky's glycerol lung broth, dextrose blood agar, Alexander-Jackson's adaptation of Bushnell's poi agar, Petragnani, Lowenstein-Jensen, Dorset egg media, Witte's peptone, Difco's bactopeptone, Armour's peptone, a Merck peptone and Fairchild's peptone.

METHODS OF IDENTIFYING CRYPTOCIDES

This invention also involves a test that will show the existance of a neoplastic disease before the tumor exists, or the existance of a chronic underlying infection in man and/or animal. Until now any aberrant symptom of a patient has to be evaluated in the light of a latent cancer until it was ruled out. A fever of unknown origin could turn out to be a sarcoma somewhere in the body made manifest weeks later after much laboratory work and X-rays. By then, it was already too late, to do anything. Even if it had been known that cancer was imminent there was no treatment. There was nothing to do but wait until a tumor presented itself and then attempt to cut it out or destroy it by radiation or chemicals. (Applicants' invention involves a cure for such cancer.)

Tests for determining the presence of cancer such as the Pap smears tests have serious problems associated therewith. In the Pap smears tests, the body cells that are cast off from the uterus, cervix and vagina are smeared from the cervix, are placed on a silde and stained. Not only is the presence of cancer cells detected but the amount of estrogen in the body is indicated by the size and shape of the nucleus of the cell in relation to the cytoplasm. This test is useful in determining the stage of menopause in women. Unfortunately, when the smear for cancer is positive, the cancer is already there. However, it does permit early detection of some kinds of cancer of the female reproductive organs. The same method of cell determination is now applied to a number of other sites such as lung and stomach.

As cancer is an infection, surgery, radiation and chemicals cannot eradicate a continuing infectuous process. For example, cobalt machines may reduce the size of tumors but contribute very little to the long-term cure of the disease.

The test of this invention allows a screening program of the entire poputation by means of routine blood cultures to determine the presence of the cryptocides bacteria correlated with evaluation of blood smears and related to immune competency by various methods of antigen-antibody determination.

There are a number of identifying biochemical tests that can be applied but these are too time-consuming and expensive for a routine laboratory. In the dying patient, a few drops of blood taken from the antecubital vein of the arm will grow out furiously on direct plating on the solid blood plates. Usually, isolation from blood is done by placing ony a few drops of blood, about five, in the bottom of a peptone-broth tube, and incubating. The organisms can be readily recognized either in hanging drops of the living cultures or by appropriate staining. The organisms grow up the side of the tube forming a lacy pattern and then produce a pellicle or doily on the surface. These usually signify the presence of motile rods. This is a good stage from which to make a vaccine. As the pellicle ages it has a tendency to drop into the tube again the spore stages are then formed. The spores cannot be used for vaccines as it is almost impossible to kill them. The liquid cultures will often transfer to solid media plates. Applicants' sensitive peptone broth for primary isolation is useful, and it can be obtained from the Colorado Serum Company in Denver, Colo. Dr. Diller's paper gives the various methods of isolation using the technique of Von Brehmer, Glover, Seibert and others. Applicants have also used synthetic broh media for primary isolation but these proved to be too toxic on animal experimentation.

There are several other ways of making primary isolations of the cryptocides. Sterilely obtained tumor tissue fresh from the operating room can be placed into liquid media and later transferred to solid blood plates. Some people have ground up the tumors, filtered them and then cultured them. This is difficult because of the problem of maintaining sterility. These methods led to the recovery of the specific microorganism, the cryptocides. Still others have made various extractives of the tumors with alcohol, acetone or other solvents and used these for the vaccine. Another method is to grow the organism from one of its favored spots, the roots of infected teeth or tonsils. However, the mouth contaminants must be eliminated. Still another way is to dilute the patient's blood with equal parts of distilled water in order to disrupt the red cells wherein the parasites are contained as well as in the serum. The tubes are lightly boiled over an open flame two or three times and then incubated for eight to twelve days. Intervening examination of the blood will reveal the rate of growth. When the growth is abundant, usually in ten to twelve days, the blood can be filtered to remove larger particles, then formalinized, standardized and tested for viability. This method may have some advantages over the whole-cell antigens obtained by the Crofton method, because the whole-blood cultures will also contain toxins and antitoxins as well as many of the minute forms which do not grow out on artificial media. This is the German method.

The following is a description of applicants' test method for the quick detection of the presence of the chorionic gonadotropic hormone (which is produced by cryptocides) in urine which indicates the existence of a chronic underlying infection in tissue and blood which produces the chorionic gonadotropic hormone, thus eliminating the need for study of individual colonies. This test can be of great importance to the medical profession, particularily in determining the presence of cancer or the likelihood of cancer proliferation. The test can be used in man and animal.

Applicants theorize that the abnormal production of the steroid chorionic gonadotropic hormone, keeps the cancer cells growing. Chorionic gonadotropic hormone is made by the microbe Cryptocides.

This tool allows the diagnosis and prognosis of chronic underlying infection or condition. Treatment can follow.

Describing the diagnoistic test, the way that applicants have found to indicate whether or not choronic gonadotropic hormone is present in the urine is: to take a predetermined amount (usually 10 ml.) from a urine specimen of the person or animal; prepare a blood culture using the urine sample; allow the blood culture to set (e.g., one day); take a predetermined amount (e.g., 3 to 5 drops) from the blood culture and directly place it in the peptone broth described elsewhere herein; and incubate (e.g., at 37° C. for 24 hours) the peptone broth. Blood plasma or serum can be used in a suitable container such as a test tube. Blood is its own media and no media need be added to it. This test procedure will give a negative or positive result depending upon the absence or presence, respectively, of chorionic gonadotropic hormone in the urine speciment. (It should be noted that minimal essentially, undetectable amounts of chorionic gonadotropic hormone may be present in the urine due to the presence of pathologically insignificant amounts of Cryptocides that are universally present in man and animal.) A positive indication (colony growth) will occur, if it is going to at all, in approximately ten days.

(The microorganism from the colonies from the urine-blood cultures may be tumorogenic and antibiotic.)

Negative, e.g., hormone, indications are always obtained when the sample from the blood specimen is first cultivated on a plate (e.g., agar) and then the colony is placed in the peptone broth. Negative indications are always obtained when the urine is culture on a blood plate (i.e., media has been added) and the colony is then placed (e.g., place blood plate with colony between fingers and squeeze over top of the broth test tube) in the peptone broth. In both instances negative indications are present even when more than normal amounts of chorionic gonedotropic hormone are present in the urine. Proper postivie indications are obtained when blood in test tube is used, but improper negative indications are obtained when blood in plates using a solid media is used. It has been reported that Cryptocides is anaerobic, which may explain the aforegoing. Also there may be present a mixture of phases of the microbe due to the pleomorphic nature of microorganism.

A positive indication means that the person or animal from whom the urine specimen was taken has a chronic underlying disease or infection, such as, cancer. This test can be used to detect all of the above listed neoplastic diseases.

Describing the prognostic test, the same procedure is used as described above for the preparation of the incubated peptone broth. Any resultant positive indication is measured conventionally for intensity or magnitude and/or length of duration of such positive indication. This gives results or measurements that can be compared with prior or future results or measurements from other incubated peptone broths made from the same patient. The prognostic test gives qualitative and quantitative results.

Since the presence of the bacterium can be proven by the product it makes, if the patient is well, the bacterium is attenuated (surpressed) and does not make significant amounts of the product. When the patient gets worse, cryptocides makes more chorionic gonadotropic hormone so prognostic tests can successively be made.

Corroboration was achieved by passing cultures, having positive indications, from primary blood isolates into the next test tube with the presence of blood. The passed cultures were allowed to grow until visible growth was seen. The growth was tested and it gave positive indications.

Another test for determining or detecting the presence of chorionic gonadotropic hormone which indicates the presence of a chronic underlying disease or infection in blood and tissue which produces the chorionic gonedotropin hormone involves a skin test. The vaccine described above is subcutaneously placed under the skin. If a welt appears, it is a positive indication that chorionic gonadotropin hormone is present and that a chronic underlying disease or infection exists in the patient.

A variation of the above skin test involves conventionally extracting a tuberculin-like substance from the vaccine described above, and subcutaneously inserting the extracted substance. If a welt appears, it is a positive indication that chronic gonadotropic hormone is present and that a chronic underlying disease or infection exists in the patient.

The urine test is the preferred detection test.

Applicants' urine test is exquisitively sensitive to a chorionic gonadotropic hormone—there are no interferring substance In other words, applicants' urine test is specific to chorionic gonadotropic hormones—it is a serological, higly specific test.

The urine speciments from seven cancer patient were each placed into separate test tubes containing only A-J peptone broth as the medium. There was specific growth in each test tube. The colonies were removed in each instance and were subjected to separation (extraction) processes until only the microorganism was left. Each of the seven isolated microorganism specimens were placed in separate test tubes containing only A-J peptone broth (no blood or agar was used). In each of the seven tubes, a positive reaction was obtained confirming the fact that the microorganism which produces chorionic gonadotropic hormone was present.

Applicants do not known of any other microorganisms besides Cryptocides which produces chorionic gonadotropic hormone, which gives a positive result in applicants' urine test.

It is known that the standard pregnancy test will give a positive indication when chorionic gonadotropic hormone is present. It is also known that a positive indication can be obtained in the pregancy test from aspirin.

Some state that cancer is essentially a cesspool for the collection of microorganisms, but applicants have found that only Cryptocides causes cancer and it is the only microorganism which produces chorionic gonadotropic hormone. Dr. Ross and others have stated in several instances that chorionic gonadotropic hormones are produced when a patient has cancer and that the chorionic gonadotropic hormone emanates from cancer.

Applicants have found that the chorionic gonadotropic hormone and/or biologically related hormones and sterols which yield a positive indication in a standard pregnency test and which can be identified by gas chromatography emanates from Cryptocides, which causes the cancer. An example of such a biologically related sterol are the phytosterols. An example of such a pregnency test is Walpole's "UCG-Test" pregnancy test which detects human chorionic gonadotropic immunologically in the urine of pregnant women.

Dr. Ross's tests used blood and found the presence of chorionic gonadotropic hormone. These are called the L-tests. Applicants are able to detect cancer by detecting the presence of chorionic gonadotropic hormone in urine. Applicants' can use their test in a diagnostic sense, that is, it can be used to determine if cancer is present. Applicants' can also use their urine test in a prognostic sense, that is, they can use it to see whether or not the amount of chorionic gonadotropic hormone has increased or decreased, and can use it to indicate the treatment to be used (depending on whether the patient's condition is better or worse).

Lactrile states that the chorionic gonadotropic hormone which is in the embryo stage is different from the other stages. Applicants' urine test detects chorionic gonadotropic hormone regardless of the stage it is in. (Kitts stated that all of the cancer cells are in the first stage).

Chorionic gonadotropic hormone is a water soluble, gonadstimulating glycoprotein.

VACCINE PREPARATION

Researchers for a number of decades have been seeking tumor antagonists not only in the form of antibiotics, which are chemicals secreted by other microorganisms, but through potential immunization by the use of other microorganisms. These biologicals are in sharp contrast to the chemotherapeutic agents that seek to destroy the dividing tumor cell regardless of the entailed immune suppress Applicants have used the causative agent itself as a menas of immunization.

Applicants have prepared and used an autogenous vaccine for the treatment of chronic, ongoing infections. Customarily the vaccines are prepared from urine, nasal, throat and bowel secretion as well as from various tissues and other secretions. The vaccines are used for the building up of immunity in the chronically ill patient who suffers from a failure to produce immune bodies against his chronic infection. This state of nonresponse is called immunoincompetence. Applicants do not represent to the cancer patient that the use of autogenous vaccine is proposed for the treatment of cancer but for their underlying failure of immune competence. In many cancer patients applicants do not use autogenous vaccine. The use of vaccines must be carefully weighed in the evaluation of the patients' immune status. In some cases the use of vaccines are actually contraindicated. In the seriously ill cancer patient the most important thing is to raise the patient's immunity by the use of fresh whole blood transfusions from suitable donors, and by the use of antibodies such as gamma globulin. The next most important thing is to treat their chronic underlying infection whatever it may be with suitable antibiotics. The removalof harmful substances from the diet is essential as well as the addition of needed vitamins and nutriments that may be lacking in the seriously ill because of lack of appetite and weight loss and faulty diet. Applicants do not believe that vaccines can cure the cancer patient. It is one of the modalities used for the chronically ill whatever their disease in the effort to restore their resistance to an ongoing; underlying chronic disease.

It is now incontrovertible that the cancer disease results in the loss of immunity yet it is treated with radiation which destroys immunity and with drugs which encourage cancerous growth. An abstract of "Carcinogenicity Studies of Clinically used Anticancer Agents", D. P. Griswold, J. D. Prejean, A. E. Casey, J. H. Weisburger, E. K. Weisburger, H. B. Wood, Jr., and H. L. Falk. Southern Research Institute, Memorial Institute of Pathology and Baptist Medical Center, Birmingham, Ala. 35205, and National Institutes of Health, Bethesda, Md. 20014, shows a number of drugs, which produce cancer in experimental animals, yet whose use is advocated by a government agency and the medical profession. Such drugs include Melphalan, Chlorambucil, uracil mustard, Natulan, dimethyltriazenoimidazole carboxamide, and 1,3-bis (2-chloroethyl-) and 1-(2-chloroethyl)-3-cyclohexyl-1-nitrosourea. Some of these are so-called anticancer drugs. Tumors of several types and at a variety of sites were seen in mice and rats during a testing of such drugs for carcinogencity.

Applicants repeat that they do not treat cancer with vaccines, use autogenous vaccines obtained from the patients' own tissues and body fluids to treat an underlying chronic infection. These organisms are not present in cancer alone but also in a host of collagen diseases and in healthy carriers as well, and that the use of vaccines for chronic disease states is an accepted modality in therepeutic medicine. Use of applicants' autogenic vaccine is therefor beneficial to a patient whether or not the patient has cancer. However, by giving the patients good nutrition, by helping them fight off chronic infection, and by using any and all accepted modalities that may be helpful, applicants assist the patients in throwing off their diseased condition, whatever it may be.

The production of vaccines from blood cultures is a rather long and tedious procedure. Applicants use the following method for making autogenous vaccines from urine. Applicants use sheep cell blood agar with phenyl ethyl alcohol, which inhibits the growth of *E. coli*, a common contaminant. Either the patient leaves the urine as directed with a testor or follows these directions at home:

1. Boil a screw-top bottle and top for twenty minutes. Let it cool. Remove with sterile tongs which have been boiled or disinfected in rubbing alcohol.
2. Take a bath. If a female, take a douche and wash off thoroughly.
3. Using three balls of sterile cotton wash off from front to back three times over the perineum with either Phisohex or some other mild disinfectant such as St 37. If a male, pull back the foreskin and wash throughly three times separately with each of the three cotton balls.
4. Start the urine stream over the toilet bowl and then catch the midstream into the sterile bottle without contaminating the inside. Be careful to keep the fingers out of the inside of the screwtop cap. Tighten the cap throughly to prevent leakage.

When the urine is received in the laboratory it is streaked onto the sterile blood plates using sterile swabs. The plates are then incubated in the usual way. Generally within 12 hours small colonies have formed. When these have been properly identified by allowing the growth to continue for a day or two to be sure that the characteristic colonies are present, then a single colony is studied by Ziehl-Neelsen stain, Kinyoun type, for acid fastness and the characteristic morphology. Then a single, identified colony is spread on one or two additional plates where they are incubated until sufficient growth has accurred. Stained preparations are again examined. The colonies are then swabbed off into a 2 percent phenol solution and permitted to stand overnight. Then after about eight hours, the phenolized cultures are diluted to 0.5 percent phenol. It requires about two weeks to complete the sterility tests and to make several dilutions according to government regulations. Autogenous vaccines tailored for each individual are prepared, but this procedure is not so limited. The vaccines are made up into 10 million, 100 million, and 1,000 million ($=1$ billion) organisms per c.c. The lowest amount, 10 million organisms per cc, is used as the starting bottle for progressive immunization. Doses are taken every three to five days depending on the reaction. It is wise to start with 0.1 cc by subcutaneous injection of the lowest amount and observe for evidence of redness or soreness at the site of the injection or symptoms of hpersensitivity such as mild fever, lalaise, or muscle or joint pains. if there is a mild reaction, the patient waits until it subsides. before repeating the same dose or smaller in three to five days by mouth. If there is no reaction, then the dose is increased by 0.1 cc to 0.2 cc and administered first by subcutaneous and then orally in three to five days. The third week, the dose is increased again by 0.1 cc to 0.3 cc subcutaneously and repeated orally again in three to five days. The oral dose is taken under the tongue and held in the mouth for absorption. The vaccine is increased in this manner until twenty drops are taken. Then the next higher dilution of organisms is started in bottle number two or 100 million organisms per cc. The starting dose is only 0.1 cc since the second dilution is ten times as strong as the first one. Again the doses are increased gradually and so on with the other bottles of the vaccines. A vaccine usually lasts six months but if there is quite a change in the character of the organisms under treatment the occasionally it is good to prepare a new vaccine in three months. This method just described is applicants' preferred method of preparation of autogenous vaccines and their administration.

The single most important factor in the presentation of vaccines is to rule out common contaminents. The colonies can be entirely confluent in severely infected hosts so that a transplant must be made in order to isolate individual colonies for study. The typical colony has an umbonate (fried egg) shape and may or may not be hemolytic. The colonies may also be wrinkled or smooth, china white or pale tan and even pale pink or orange when grown in the dark. The slides are made by lightly wiping a culture from the plate with a sterile cotton swab or with a platinum loop onto the surface of the glass slide and fixing it with gentle heat. One colony only should be selected and a cross-section should be studied by taking samples from the center outward to the periphery to obtain the different pleomorphic stages. If the material is handled gently they ray formation of the growth will not be broken up. The Kinyoum modification of the Ziehl-Neelsen stain is used since it can be applied in the cold for five minutes and does not require heating. The red dye is washed off with sterile distilled water and the slide is then briefly decolorized with 1 percent hydrochloric acid in 70 percent alcohol. The Cryptocides organisms are more sensitive to decolorization by acid-alcohol than the tubercle bacillus. The slide is washed again and the methylene blue counterstain is applied, 6 to 8 drops of normal (4%) of sodium hydroxide are added. After 30 seconds it is washed off. After the slide is air-dried it is ready for examination under the light microscope at not less than $\times 800$ with oil immersion. If slides are prepared from tissue impression smears of tumors, the same procedure is followed but Alexander-Jackson's triple stain may be applied to duplicate slides in order to differentiate the non-acid fast forms of Cryptocides from common contaminants. At times, the Cryptocides organism is not acid-fast in some stages of its growth.

Usually the organism isolates out in the coccal form which has led many investigators to believe they are dealing with a staphylococcus. However, the cocci will be both acid-fast and non-acid-fast and will vary greatly in shape from the very small to the large globoidal or sac forms which often stain blue and appear to be spilling out the red acid-fast cocci much as marbles out of a bag. In addition, the cocci appear to split longitudinally into small rods. The cocci, after a period of time, have small filaments spouting from them which turn into rods that are red or acid-fast. If the culture is not mutilated by rough handling, often the large tublar forms can be seen which are observed by darkfield microscope in fresh blood. These are very delicate and disrupt easily. The ray formation may also be apparent but the sheath is extremely diaphanous and is destroyed often in the staining process. Sometimes the cancer organism can isolate out primarily as a rod or even as a branching hyphal form. At other times clublike bodies are seen which are blue in color and contain the acid-fast bodies within them. It is very important to study a number of the colonies on the plates and to be sure that the various transitional forms of the organism can be seen in one isolated colony. Only then may the organism be grown in sufficient amount to harvest for the vaccine. All of this work requires careful examination and experience to be sure of the growth pattern and morphology of the Cryptocides.

The organisms isolated from the urine cultures have been classified under various names such as staphylococcus epidermidis and enterococcus fecalis, in other words, common organisms found on the skin and in the bowel. However, by careful sterile methods microorganisms are found to be growing from the urine in great abundance. Microbiologists are still debating the nature and classification of these organisms. A recent paper, which appeared in Transactions of the New York Academy of Sciences, by Dr. Florence Seibert, claims that these isolates from her material which yield certain supposedly well-known microorganisms are not the standard well-recognized types at all but the acid-fast organisms which we have classified as the Cryptocides. Microbiologists who examined applicants' urine cultures state that there are a variety of organisms in applicants' urine vaccines. What is known is that these organisms occur in large numbers and are often hemolytic (destructive of red blood cells). Very possibly urine cultures contain a mixture of whatever microbes that happen to filter through the kidneys from distant body foci. Applicants use the mixture in vaccines only as nonspecific immune booster in chronic disease.

The vaccine can be prepared by the following preferred method. To 10 cc of heparinized freshly-drawn sterile blood add 10 cc sterile distilled water. Heat over the Bunsen burner to boiling several times (to break the red cells). Incubate for 10 to 12 days at 37° to 38° C. This gives the growing culture without addition of media, since blood acts as its own medium without the addition of anything else. Add 4 percent formalin (formaldehyde) to inactivate (kill) the *P. Cryptocides*. The admixture is put through a microfilter to remove the dead or microorganisms. The live attenuated microorganisms go through the filters. Then dilute the filtrate with sterile saline solution until the final solution contains 1% formalin. This is then tested for sterility and than can be used as an autogenous vaccine.

The autogenous vaccine can be used to immunize against underlying chronic diseases or infections, or neoplastic diseased which produce choroninic gonedotropic hormone and/or biologically related hormones and sterols which yield a positive indication in a standard pregnancy test and which can be identified by gas chromatography and which are caused by Cryptocides.

EXAMPLE

Materials and Methods

Female mice of strain A/He, 2 months old, were divided into 4 groups of 16 animals each. The average body weight for each group was 28.1 g. Animals all received 12 intrapertoneal injections, 3 injections per week for 4 weeks (Mondays, Wednesdays and Fridays). Sterile disposable plastic syringes fitted with 25-gauge needles were used for each injection.

The mice were housed in plastic shoe box-type cages, 8 per cage, and fed a standard Teklad mouse diet and water ad libitum. They were weighed before each injection and then weekly following the injection period. The injections contain the reddish-brown crystalline material extracted from broth containing organisims within the scope of this invention.

| Dosages used | Dose/Injection |
|---|---|
| N.C. var. | 0.13 mg/0.1 ml |
| Control | 0.13 mg/0.1 ml |
| #6 | 1.40 mg/0.1 ml |
| #5 | 0.28 mg/0.1 ml |

At 20 weeks after the last injection, the mice were killed by cervical dislocation. Necropsies were performed and the lungs removed and fixed in Tellyesniczky's fixitive for 24 hours. The number of tumor nodules on each lung was determined after fixation by counting with the naked eye.

The animals tolerated the materials extremely well and no adverse effects were encountered.

It will be apparent that the present invention may be employed in various embodiments as desired by those skilled in the art and it is not intended to limit the invention by the specification; rather to include all such equivalents as come within the scope of the appended claims.

We claim:

1. A method of preparing an autogenous vaccine for immunization against neoplastic diseases characterized by the presence of a *Progenitor cryptocides* organism identified by ATCC 31,874, which comprises:
   (a) admixing a sterile blood sample containing *Progenitor cryptocides* with sterile distilled water;
   (b) incubating the admixture;
   (c) killing or inactivating the *Progenitor crytocides* in the admixture;
   (d) microfiltering the admixture to remove blood cells, and
   (e) diluting the filtrate containing the attenuated *Progenitor cryptocides* with a sterile saline solution, thereby forming autogenous vaccine.

2. A method of preparing an autogenous vaccine for use in improving the immunocompetence of animals affected with a neoplastic disease which results in the production of the hormone chorionic gonadotropin as a nonspecific immune booster, comprising:
obtaining a sample of body tissue or body fluid containing the microorganism *Progenitor cryptocides,*
culturing the sample under suitable conditions conducive for growth of colonies of microorganisms contained in the sample,
identifying those colonies characteristic of the *Progenitor cryptocides* microorganism,
isolating and culturing those identified colonies,
killing the *Progenitor cryptocides* microorganism, and
diluting the killed microorganism with a sterile saline solution to form the autogenous vaccine.

3. The method of claim 2 wherein the sample is urine.
4. The method of claim 2 wherein the sample is a bowel secretion.
5. The method of claim 2 wherein the sample is blood.

* * * * *

UNITED STATES PATENT AND TRADEMARK OFFICE
CERTIFICATE OF CORRECTION

PATENT NO. : 4,692,412  Page 1 of 5
DATED : September 8, 1987
INVENTOR(S) : Virginia W. Livingston et al.

It is certified that error appears in the above-identified patent and that said Letters Patent is hereby corrected as shown below:

Col. 1, line 40, change "erytheuratosis" to -- erythematosis --;
Col. 1, line 42, change "collogen" to -- collagen --;
Col. 1, line 58, change "fact" to -- fast --;
Col. 2, line 22, change "Ziel" to -- Zehl --;
Col. 2, line 44, change "pneumonilike" to -- pneumonialike --;
Col. 3, line 6, change "socalled" to -- so-called --;
Col. 3, line 31, change "a" to -- an --;
Col. 4, line 5, change "expecially" to -- especially --; change "cytosinguanine" to -- cytosine-guanine --; and change "mu" to -- nu --;
Col. 4, line 8, change "wals" to -- walls --;
Col. 4, line 20, change "filted" to -- filtered --;
Col. 4, line 40, change "effect" to -- affect --;
Col. 5, line 43, change "bessels" to -- vessels --;
Col. 5, line 55, change "postmorten" to -- postmortem --;
Col. 5, line 58, change "carbon" to -- carbul --;
Col. 6, line 17, delete "in";
Col. 6, line 31, change "deposity" to -- deposits --;
Col. 7, line 52, change "leukosos" to -- leukosis --;

UNITED STATES PATENT AND TRADEMARK OFFICE
CERTIFICATE OF CORRECTION

PATENT NO. : 4,692,412

DATED : September 8, 1987

INVENTOR(S) : Virginia W. Livingston et al.

It is certified that error appears in the above-identified patent and that said Letters Patent is hereby corrected as shown below:

Col. 8, line 3, change "mn" to -- m --;

Col. 8, line 33, change "sterlized" to -- sterilized --;

Col. 8, line 51, change "that" to -- than --;

Col. 9, line 1, change "tp" to -- to --;

Col. 9, line 12, change "B" to -- F --;

Col. 9, line 62, change "acidfied" to -- acidified --;

Col. 10, line 53, change "and" to -- an --;

Col. 11, line 45, change "an" to -- and --;

Col. 12, line 20, change "evaluted: to -- evaluated --;

Col. 13, line 9, change "erythocytes" to -- erythrocytes --;

Col. 14, line 1, change "tubles" to -- tubules --;

Col. 14, line 7, change "perparations" to -- preparations --;

Col. 14, line 35, change "dextoxifying" to -- detoxifying --;;

Col. 14, line 37, change "autogeneous" to -- autogenous --;

Col. 14, line 53, change "autogeneous" to -- autogenous --;

Col. 14, line 55, change "temperatures" to -- temperature --;

Col. 15, line 19, change "succeptible" to -- susceptible --;

Col. 15, line 35, change "biologic" to -- biologicals --;

Col. 15, line 41, change "funtcion" to -- function --;

UNITED STATES PATENT AND TRADEMARK OFFICE
CERTIFICATE OF CORRECTION

PATENT NO. : 4,692,412  
DATED : September 8, 1987  
INVENTOR(S) : Virginia W. Livingston et al.

Page 3 of 5

It is certified that error appears in the above-identified patent and that said Letters Patent is hereby corrected as shown below:

Col. 15, line 46, change "with" to -- which --;

Col. 15, line 49, change "pituary" to -- pituitary --;

Col. 15, line 58, insert -- but also -- between "effects" and "by";

Col. 15, line 64, after "poisons" insert a period;

Col. 15, line 66, change "whereever" to -- wherever --;

Col. 15, line 67, change "interstital" to -- interstitial --;

Col. 16, line 10, charge ";" to --: --;

Col. 16, line 17, change "glutethimidine" to -- glutethimide --;

Col. 17, line 63, change "while" to -- white --;

Col. 18, line 12, change "blendor" to -- blender --;

Col. 18, line 14, change "an" to -- and --;

Col. 18, line 16, change "pound" to -- pounds --;

Col. 18, line 59, change "infectuous" to -- infectious --;

Col. 18, line 64, change "poputation" to -- population --;

Col. 19, line 7, change "ony" to -- only --;

Col. 19, line 25, change "broh" -- broth --;

Col. 20, line 6, change "diagnoistic" to -- diagnostic --;

Col. 20, line 7, change "choronic" to -- chorionic --;

UNITED STATES PATENT AND TRADEMARK OFFICE
CERTIFICATE OF CORRECTION

PATENT NO. : 4,692,412

DATED : September 8, 1987

INVENTOR(S) : Virginia W. Livingston et al.

Page 4 of 5

It is certified that error appears in the above-identified patent and that said Letters Patent is hereby corrected as shown below:

Col. 20, line 21, change "speciment", to -- specimen --;
Col. 20, line 42, change "gonedotropic" to -- gonadotropic --;
Col. 20, line 43, change "postivie" to -- positive --;
Col. 20, line 67, change "surpressed" to -- suppressed --;
Col. 21, line 13, change "gonedotropin" to -- gonadotropic --;
Col. 21, line 16, change "gonadotropin" to -- gonadotropic --;
Col. 21, line 29, after "substance" insert a period;
Col. 21, line 31, change "higly" to -- highly --;
Col. 21, line 32, change "speciments" to -- specimens --;
Col. 21, line 44, change "known" to -- know --;
Col. 21, line 64, change "pregnency" to -- pregnancy --;
Col. 21, line 68, change "pregnency" to -- pregnancy --;
Col. 22, line 32, change "suppress" to -- suspression. --;
Col. 22, line 33, change "menas" to -- means --;
Col. 22, line 56, change "removalof" to -- removal of --;
Col. 22, line 58, change "nutriments" to -- nutrients --;
Col. 22, line 63, delete ";"
Col. 23, line 18, insert -- but -- after "vaccines";
Col. 23, line 24, change "therepeutic" to -- therapeutic --;
Col. 23, line 66, change "accurred" to -- occurred --;

UNITED STATES PATENT AND TRADEMARK OFFICE
CERTIFICATE OF CORRECTION

PATENT NO. : 4,692,412
DATED : September 8, 1987
INVENTOR(S) : Virginia W. Livingston et al.

It is certified that error appears in the above-identified patent and that said Letters Patent is hereby corrected as shown below:

Col. 24, line 15, change "hpersensitivity" to -- hypersensitivity --;
Col. 24, line 15, change "lalaise" to -- malaise --;
Col. 24, line 33, change "the" to then --;
Col. 24, line 39, change "contaminents" to -- contaminants --;
Col. 24, line 53, change "they" to -- the --;
Col. 25, line 17, change "tublar" to -- tubular --;
Col. 25, line 67, delete "or";
Col. 26, line 3, change "than" to -- then --;
Col. 26, line 6, change "diseased" to -- diseases --;
Col. 26, line 6, change "choroninic" to -- chorionic --;
Col. 26, line 6, change "gonedotropic" to -- gonadotropic --;
Col. 26, line 18, change "intrapertoneal" to -- intraperitoneal
Col. 26, line 27, change "organisims" to -- organisms --.

Signed and Sealed this

Fifteenth Day of November, 1988

Attest:

DONALD J. QUIGG

Attesting Officer          Commissioner of Patents and Trademarks